(12) United States Patent
Al-Marzouqi et al.

(10) Patent No.: US 10,767,267 B2
(45) Date of Patent: Sep. 8, 2020

(54) ANTICORROSION MATERIAL PRODUCED FROM DATE PALM TREE WASTE

(71) Applicant: UNITED ARAB EMIRATES UNIVERSITY, Al Ain (AE)

(72) Inventors: Ali Humaid Mohamed Hassan Al-Marzouqi, Al Ain (AE); Nour Shehadeh Abdelrahman, Al Ain (AE); Aysha Mohammed Al Ahbabi, Al Ain (AE); Aamna Ebrahim Almusharrakh, Al Ain (AE); Amna Sultan Al Ali, Al Ain (AE); Sara Hareb Al-Ketbi, Al Ain (AE)

(73) Assignee: United Arab Emirates University, Al-Ain (AE)

( * ) Notice: Subject to any disclaimer, the term of this patent is extended or adjusted under 35 U.S.C. 154(b) by 68 days.

(21) Appl. No.: 16/022,639

(22) Filed: Jun. 28, 2018

(65) Prior Publication Data

US 2020/0002820 A1 Jan. 2, 2020

(51) Int. Cl.
C23F 11/12 (2006.01)
C07G 1/00 (2011.01)
A01H 6/00 (2018.01)
C09D 5/08 (2006.01)
C23F 11/16 (2006.01)

(52) U.S. Cl.
CPC ............... *C23F 11/12* (2013.01); *C07G 1/00* (2013.01); *A01H 6/00* (2018.05); *C09D 5/08* (2013.01)

(58) Field of Classification Search
CPC .......... C23F 11/12; C23F 11/164; C07G 1/00; A01H 6/00; C09D 5/08; C09D 5/082
See application file for complete search history.

(56) References Cited

U.S. PATENT DOCUMENTS 4,892,588 A 1/1990 Dilling et al.
9,404,221 B2 8/2016 Hagiopol et al.

FOREIGN PATENT DOCUMENTS

CN 103102826 A 5/2013
CN 103102834 A 5/2013
CN 103275527 A 9/2013

OTHER PUBLICATIONS

Reddy et al., "A comparison of microstructure and adsorption characteristics of activated carbons by CO2 and H3PO4 activation from date palm pits", New Carbon Materials (2012), vol. 52, No. 5, pp. 344-351.
Tappi Method T 222, "Acid-insoluble lignin in wood and pulp (Reaffirmation of T 222 om-02)", Tappi Press (2006), 14 pages.
Hu et al., Methods to Improve Lignin's Reactivity as a Phenol Substitute and as Replacement for Other Phenolic Compounds: A Brief Review, BioResources (2011), 6(3), 11 pages.
J. Thiruppathy et al., "Inhibitive Action of Calcium Lignosulfonate on the Corrosion of Mild Steel in Sulfuric Acid Medium",International Journal of Scientific Research Publications (2014), vol. 4, Iss. 9, 8 pages.

*Primary Examiner* — Andrew J. Oyer
(74) *Attorney, Agent, or Firm* — Richard C. Litman; Nath, Goldberg & Meyer

(57) ABSTRACT

Anti-corrosion material is produced from date palm tree waste by extracting lignin and modifying by sulfonation. The anti-corrosion material produced from date palm tree waste is non-toxic and effective at preventing or reducing corrosion of, for example, metals subject to corrosive environments, and particularly marine environments.

8 Claims, 1 Drawing Sheet

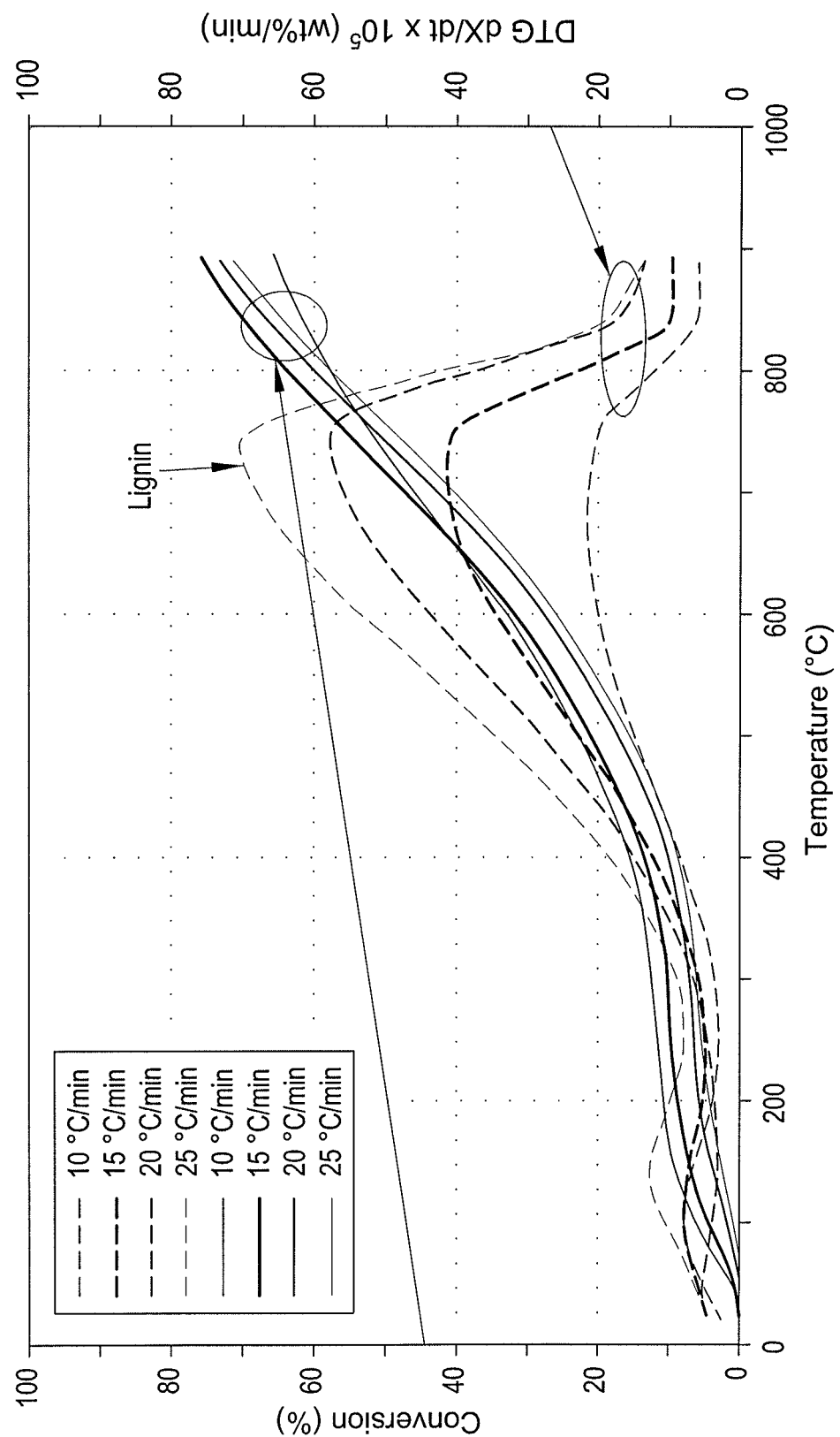

ANTICORROSION MATERIAL PRODUCED FROM DATE PALM TREE WASTE

BACKGROUND

1. Field

The disclosure of the present patent application relates to anti-corrosion material, and particularly to an anti-corrosion material produced from date palm tree waste.

2. Description of the Related Art

Lignin is the second most abundant natural polymer, typically representing 10-30% of lignocellulosic biomass. Lignin is a class of complex organic polymers that form significant structural materials in the support tissues of vascular plants and some algae. Lignin is particularly significant in the structure of cell walls, specifically in wood and bark, as it lends rigidity and does not rot easily.

Chemically, lignin is a three-dimensional, highly crosslinked macromolecule composed of three types of substituted phenols, including: coniferyl, sinapyl, and p-coumaryl alcohols. Lignin forms by enzymatic polymerization of these substituted phenols, yielding a massive number of functional groups and linkages. Hence, lignin differs significantly from species to species, and even from tissue to tissue within the same plant. This diversity results in many processes for extracting lignin from a given plant or plant tissue, producing lignin of varying form, chemical composition, and properties.

United Arab Emirates and the surrounding Gulf nations are home to tens of millions of date palm trees, particularly of the species *Phoenix dactylifera* L. A single date palm tree produces approximately 20 kg of waste leaves annually, resulting in a waste biomass composed primarily of lignocellulosic materials. This biomass is primarily made up of carbohydrates containing cellulose and hemicellulose, attached with lignin. Thus, the date palm tree population in the UAE alone represents a potentially abundant natural source of lignin for use in any number of value-added end products. However, at this time, most date palm tree waste is converted to compost or burned for heat, as reliable processes for extracting lignin from date palm tree waste in a condition appropriate for use in other applications are not well-known. Processes for reliably extracting lignin from the abundant biomass of date palm tree waste would therefore provide both environmental and economic advantages over present date palm tree waste disposal and usage.

One potential application of lignin is in anti-corrosive agents. Corrosion significantly impacts many fields of industry, technically and economically. As such, anti-corrosive materials appropriate for a wide range of applications are desired and are the subject of active research and development. For example, anti-corrosion materials, such as paints, for use in marine environments should ideally be nontoxic and harmless to the marine ecosystem. Studies have reported lignosulfonate useful in corrosion inhibitors. However, due to the unpredictability and technical challenges of reliably extracting lignin with well-known properties and characteristics from a given natural source, such efforts at producing lignosulfonate-based corrosion inhibiting materials typically rely on Kraft lignin or commercially purchased lignosulfonate as a source.

Thus, an anti-corrosion material produced from date palm tree waste solving the aforementioned problems is desired.

SUMMARY

The anti-corrosion material produced from date palm tree waste is made from lignin that is extracted from the waste and then converted to sodium lignosulfonate, which can be used to coat a substrate, e.g., mild steel, to protect the substrate from corrosion. Lignin is extracted from date palm waste by removing extractives, extracting the remaining biomass by Klason extraction in 72% sulfuric acid, diluting the extraction mixture to 3% sulfuric acid and refluxing for four hours. The lignin is placed in water, pH is raised to 10, the lignin is methylolated by addition of formaldehyde, sulfonated by addition of sodium sulfite, and heated to 100° C. with stirring for 3 hours. The sodium lignosulfonate product was solidified by addition of 25M sulfuric acid, washed, and dried. Mild steel immersed in the lignosulfonate resisted corrosion by acid in weight loss testing.

These and other features of the present disclosure will become readily apparent upon further review of the following specification and drawings.

BRIEF DESCRIPTION OF THE DRAWINGS

The sole drawing FIGURE is a plot of TGA (thermogravimetric analysis) and DTG (differential gravimetric) curves of extracted lignin at heating rates of 10, 15, 20 and 25° C./min.

DETAILED DESCRIPTION OF THE PREFERRED EMBODIMENTS

The anti-corrosion material or corrosion inhibitor produced from date palm tree waste is made from lignin that is extracted from the waste and then converted to sodium lignosulfonate, which can be used to coat a substrate, e.g., mild steel, to protect the substrate from corrosion. Lignin is extracted from date palm waste by removing extractives, extracting the remaining biomass by Klason extraction in 72% sulfuric acid, diluting the extraction mixture to 3% sulfuric acid and refluxing for four hours. The lignin is placed in water, pH is raised to 10, the lignin is methylolated by addition of formaldehyde, sulfonated by addition of sodium sulfite, and heated to 100° C. with stirring for 3 hours. The sodium lignosulfonate product was solidified by addition of 25M sulfuric acid, washed, and dried. Mild steel immersed in the lignosulfonate resisted corrosion by acid in weight loss testing.

The process for extracting lignin from date palm tree waste includes the following steps. (1) Biomass (i.e., date palm tree waste) was treated to make it extractive-free (free of protein, waxes and resins), and in a particular example, a 5 g biomass sample was transferred to a weighed thimble tube and extracted with 150 ml of ethanol-benzene solvent 1/2 v/v for 5 hours. (2) The residue from the above extraction process was oven-dried at 103° C. for 1 hour, cooled in a desiccator and weighed to determine the extractive-free biomass to be used for the following improved-Klason lignin extraction. (3) 1 g of the extractive free biomass produced as above was treated with 72% $H_2SO_4$ for 2 hours under stirring at 37° C. (4) The treated extractive-free biomass was then diluted to a 3% $H_2SO_4$ solution. (5) The solution was refluxed at 80° C. for 4 hours, resulting in a hydrolyzed residue. (6) The hydrolyzed residue is filtered on a Buchner funnel and washed free of acid by means of hot water. (7) After filtration, the isolated insolubles, i.e., extracted lignin, was oven-dried at 105° C. for 1 hour and cooled in a desiccator until a constant weight was obtained, the difference in weight before and after oven-drying giving the amount of extracted lignin.

It is noted that, in step 3, a temperature of 37° C. was used to break the linkages between lignin, cellulose and hemicellulose and to remove the cellulose and hemicellulose, the lignin being insoluble in sulfuric acid, in order to extract pure lignin from the date palm waste. When a temperature of 20° C. was used, as in the traditional Klason method, cellulose and hemicellulose were still present in the product. Lignin content and structure differs from one species to another, and even from one tissue to another in the same plant (the present exemplary extraction being performed on *Phoenix dactylifera* L., obtained from the United Arab Emirates); hence, the properties of the extracted lignin may vary according to the source of the date palm tree waste. Also, the extracted lignin may require unexpectedly different experimental conditions from what is otherwise known. The purity of extracted lignin was confirmed by TGA as shown in the sole drawing FIGURE.

The extracted lignin was converted to sodium lignosulfonate by the following procedure. The main method of sulfomethylolation of extracted lignin involves a three-step process. In particular, phenol components of the extracted lignin are ionized at an alkaline pH, the lignin is methylolated (also referred to as hydroxymethylation, i.e., a hydroxymethyl [—CH2OH] functional group is added to the lignin) by addition of formaldehyde in alkaline media, and the lignin is sulfonated by addition of sodium sulfite. Specifically, (1) 5 g of extracted lignin and 100 mL of deionized water were added into a 250 mL three-neck flask equipped with a stirrer, a thermometer, and a reflux condenser. (2) The pH was adjusted to 10 by addition of 0.5 M NaOH solution. (3) 1.0 mL of 0.123 M formaldehyde was added to the solution. (4) 4 g of 0.317 M sodium sulfite was added to the solution to form a reaction mixture. (5) The reaction mixture was heated to 100° C. (6) The reaction mixture was stirred for 3 h at 150 rpm. (7) 25 M sulfuric acid was added in order to solidify (precipitate) sodium lignosulfonate from the reaction mixture. (8) Finally, the precipitated lignosulfonate was centrifuged, washed and dried. The resulting lignosulfonate produced was in the form of a paste capable of being spread or painted on a surface.

The composition was tested as follows. Weight loss measurements were performed using mild steel (MS) specimens of size 4.7 cm×1.5 cm×0.2 cm. The specifications of the mild steel used for weight loss analysis are shown in Table 1, as follows.

TABLE 1

Specifications of Mild Steel Samples
Mild Steel (MS)

| | |
|---|---|
| MS Density (g/cm$^3$) | 7.75 |
| Exposure Time (h) | 120 |
| Dimensions (cm) | 4.7*1.5*0.2 |
| Surface Area (cm$^2$) | 7.05 |
| Original Weight (g) | 15.258 |

For the corrosion test, the paste form of lignosulfonate prepared as described above was used (about 2 ml) to cover/coat the MS specimens with one layer on both sides. Uncoated MS specimens were used as controls. The following steps were then performed. (1) MS specimens were weighed to get an initial weight. (2) MS specimens were immersed in 1M of sulfuric acid $H_2SO_4$ solution for a period of 5 days. (3) Weight loss studies were performed at controlled temperatures of 25° C. (4) After immersion, the surface of each specimen was cleaned by distilled water and dried. (5) The dried MS specimens were weighed to get a corroded weight. (6) MS specimen corrosion was determined by weight loss and visual inspection.

The metal weight loss after performing the weight loss test can be converted to a corrosion rate, a percentage metal loss, or an inhibition efficiency (%), which are calculated according to equations (1), (2), and (3), respectively.

$$\text{Corrosion Rate } \left(\frac{mm}{yr}\right) = \frac{\text{Weight loss (g)} * K}{\text{Alloy density } \left(\frac{g}{cm^3}\right) * \text{Exposed Area of Specimen (cm}^2) * \text{Exposure Time (hr)}} \quad (1)$$

where $K=8.75*10^4$ and the corrosion rate is expressed in millimeters (thickness) per year.

$$\text{Metal Loss(mm)} = \frac{\text{Weight loss (g)} * k}{\text{Alloy density } \left(\frac{g}{cm^3}\right) * \text{Exposed Area of Specimen (cm}^2)} \quad (2)$$

where $k=10$ and the metal loss is expressed in millimeters (thickness).

$$\text{Inhibition efficiency (\%)} = \frac{\text{Weight loss without inhibitor (g)} - \text{Weight loss with inhibitor (g)}}{\text{Weight loss without inhibitor (g)}} * 100, \quad (3)$$

where:

Weight loss=Original specimen weight (g)−Specimen weight after corrosion test (g). (4)

The results are shown in Table 2, below.

TABLE 2

Weight loss analysis

| | Control | Specimen coated with lignosulfonate |
|---|---|---|
| MS Weight after test (g) | 13.586 | 15.198 |
| Weight loss (g) | 1.672 | 0.059 |
| Corrosion rate (mm/yr) | 22.313 | 0.799 |
| Metal loss (mm) | 0.306 | 0.011 |
| Inhibition efficiency (%) | — | 96.417 |

The corrosion rate of the tested samples significantly decreased from 22.313 to 0.799 (mm/yr) with the addition of sodium lignosulfonate. These results indicate that the sodium lignosulfonate produced from the lignin extracted from date palm tree waste acts as a good corrosion inhibitor and can be used to protect mild steel from corrosion with an efficiency of 96.417%.

It is to be understood that the production of anti-corrosion material from date palm tree waste is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of making a sodium lignosulfonate corrosion inhibitor, comprising the steps of:
   providing a quantity of date palm tree waste;
   removing the extractives from the date palm tree waste to produce an extractive-free biomass, wherein the extractives are removed in an ethanol-benzene extraction solvent mixture;
   extracting lignin from the extractive-free biomass;
   immersing the lignin in alkaline media;
   adding formaldehyde to the lignin immersed in alkaline media to methylolate the lignin;
   adding sodium sulfite to the methylolated lignin to sulfonate the lignin, the methylolated and sulfonated lignin immersed in the alkaline media forming a reaction mixture;
   heating the reaction mixture at 100° C. with stirring for 3 hours to complete sulfonating the lignin;
   adding 25M sulfuric acid to the reaction mixture to precipitate sodium lignosulfonate;
   centrifuging, washing, and drying the precipitated sodium lignosulfonate; and
   recovering the sodium lignosulfonate in paste form.

2. The method of making a corrosion inhibitor according to claim 1, wherein said step of heating the reaction mixture at 100° C. further comprises heating the reaction mixture under reflux.

3. The method of making a corrosion inhibitor according to claim 1, further comprising the step of oven-drying solid residue obtained from the ethanol-benzene extraction solvent mixture to recover an extractive-free biomass from the date palm tree waste.

4. The method of making a corrosion inhibitor according to claim 3, wherein said step of extracting lignin from date palm tree waste further comprises the steps of:
   treating the extractive-free biomass with 72% sulfuric acid for two hours to form biomass in acid solution;
   diluting the acid solution to 3% sulfuric acid;
   heating the biomass in diluted acid solution under reflux for four hours; and
   separating acid-insoluble lignin from the refluxed acid solution.

5. The method of making a corrosion inhibitor according to claim 4, wherein said separating step comprises filtering the refluxed acid solution on a Buchner funnel to recover the acid-insoluble lignin.

6. The method of making a corrosion inhibitor according to claim 4, wherein said separating step comprises the steps of allowing residue to settle in the diluted acid solution after reflux and decanting liquid separated above the residue to recover the acid-insoluble lignin.

7. The method of making a corrosion inhibitor according to claim 4, wherein said step of treating the extractive-free biomass with 72% sulfuric acid comprises stirring the extractive-free biomass in 72% sulfuric acid at 37° C. for two hours.

8. The method of making a corrosion inhibitor according to claim 1, wherein said date palm tree waste comprises waste from *Phoenix dactylifera* L. trees grown in the United Arab Emirates.

* * * * *